(12) United States Patent
Deegan et al.

(10) Patent No.: US 8,678,996 B2
(45) Date of Patent: Mar. 25, 2014

(54) INCONTINENCE TREATMENT DEVICE INCLUDING NON-POROUS SUB-URETHRAL SLING

(71) Applicant: Coloplast A/S, Humlebaek (DK)

(72) Inventors: Christopher Deegan, North St. Paul, MN (US); Steven McClurg, Brooklyn Park, MN (US); Mark A. Moschel, New Hope, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/688,226

(22) Filed: Nov. 29, 2012

(65) Prior Publication Data
US 2013/0296638 A1    Nov. 7, 2013

Related U.S. Application Data (60) Provisional application No. 61/641,314, filed on May 2, 2012.

(30) Foreign Application Priority Data

May 1, 2012 (DK) .................. 2012 70219

(51) Int. Cl.
*A61F 2/02* (2006.01)
(52) U.S. Cl.
USPC .............................................. 600/37; 600/30
(58) Field of Classification Search
USPC ..................... 600/30, 37; 606/151
See application file for complete search history.

(56) References Cited

U.S. PATENT DOCUMENTS

| 4,552,128 A | 11/1985 | Haber |
| 5,544,664 A | 8/1996 | Benderev et al. |
| 5,620,012 A | 4/1997 | Benderev et al. |
| 5,702,397 A * | 12/1997 | Goble et al. ............ 606/232 |
| 5,746,763 A | 5/1998 | Benderev et al. |
| 5,813,408 A | 9/1998 | Benderev et al. |
| 5,836,314 A | 11/1998 | Benderev et al. |
| 5,836,315 A | 11/1998 | Benderev et al. |
| 5,842,478 A | 12/1998 | Benderev et al. |
| 5,860,425 A | 1/1999 | Benderev et al. |
| 5,934,283 A | 8/1999 | Willem et al. |
| 6,001,104 A | 12/1999 | Benderev et al. |

(Continued)

FOREIGN PATENT DOCUMENTS

| WO | 2002058564 | 8/2002 |
| WO | 2007002071 | 1/2007 |

OTHER PUBLICATIONS

Final Office Action mailed on Aug. 29, 2013 in U.S. Appl. No. 13/676,132.

(Continued)

*Primary Examiner* — Jacqueline Cheng
*Assistant Examiner* — Kaylee Wilson
(74) *Attorney, Agent, or Firm* — Coloplast Corp., Coloplast A/S; Nick Baumann (57) ABSTRACT

An incontinence treatment device includes a non-porous sub-urethral sling provided with an adjustment device. The device includes first and second anchors coupled to the sling. The second anchor includes a channel formed through the second anchor and a restrictor segment provided in the channel. The adjustment device is movable through the channel formed through the second anchor. The resistor segment is configured to resist movement of the adjustment device through the channel.

10 Claims, 6 Drawing Sheets

(56) References Cited

U.S. PATENT DOCUMENTS

| | | |
|---|---|---|
| 6,056,688 A | 5/2000 | Benderev et al. |
| 6,077,216 A | 6/2000 | Benderev et al. |
| 6,110,101 A * | 8/2000 | Tihon et al. .................. 600/37 |
| 6,904,916 B2 | 6/2005 | Bakane |
| 7,326,213 B2 | 2/2008 | Benderev et al. |
| 7,387,634 B2 | 6/2008 | Benderev |
| 7,789,821 B2 | 9/2010 | Browning |
| 2004/0173219 A1 | 9/2004 | Bakane |
| 2006/0252980 A1 * | 11/2006 | Arnal et al. .................. 600/29 |
| 2008/0167520 A1 | 7/2008 | Benderev |
| 2009/0149883 A1 * | 6/2009 | Brunsvold .................. 606/232 |
| 2009/0259092 A1 | 10/2009 | Ogdahl et al. |
| 2010/0198003 A1 * | 8/2010 | Morningstar et al. .......... 600/37 |
| 2010/0198004 A1 | 8/2010 | Moschel et al. |
| 2010/0312052 A1 | 12/2010 | Morningstar |
| 2011/0034762 A1 | 2/2011 | Paganon |
| 2011/0077455 A1 | 3/2011 | Duncan et al. |
| 2011/0306822 A1 | 12/2011 | Witzmann et al. |
| 2012/0035627 A1 | 2/2012 | Ostrovsky et al. |

OTHER PUBLICATIONS

Extended Search Report mailed on Aug. 7, 2013 in EP application No. 13166095.3.

* cited by examiner

INCONTINENCE TREATMENT DEVICE INCLUDING NON-POROUS SUB-URETHRAL SLING

BACKGROUND

Devices for treating urinary incontinence include slings, supports, artificial urinary sphincters and other devices that are implanted in a user to support and/or coapt the urethra.

A sling is a device that is surgically implanted to support the urethra and inhibit urine from undesirably leaking from the urethra. Slings are typically fabricated from mesh and are implanted through one or more incisions. The sling is secured to supporting tissue(s) and the tissue eventually grows through the mesh to support the urethra. The surgeon will peri-operatively determine and achieve the appropriate level of tension in the sling relative to the urethra that will post-operatively provide the user with a continent state.

Improved incontinence treatment devices would be welcomed by both the patient and the surgical staff.

SUMMARY

One aspect provides an incontinence treatment device including a non-porous sub-urethral sling provided with an adjustment device. The device includes a first extension member attached to a first end of the sling, a first anchor attached to the first extension member, and a first line attached to the first end of the sling and inserted through a bore formed through the first anchor. The first line includes a stop device fixed to the first line with the first anchor positioned between the stop device and the sling. The device also includes a second extension member attached to a second end of the sling, a second anchor attached to the second extension member, and a second line attached to the second end of the sling. The second anchor includes a channel formed through the second anchor and a restrictor segment provided in the channel. The adjustment device is attached to the second line and is movable through the channel formed through the second anchor. The restrictor segment is configured to resist movement of the adjustment device through the channel.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

In this specification the word "coapt" means to close or to substantially close. To coapt an opening is to bring two surfaces together in close approximation such that the gap between the two surfaces is reduced or eliminated. To coapt a urethra means to substantially yet reversibly close the urethra to impede the passage of urine and provide a person with a continent state.

In this specification a "user" is one into whom an incontinence treatment device has been implanted.

In this specification "non-porous" means a material with no through-holes. For example, while the non-porous material might include divots and/or recesses in a surface of the material, the material does not have holes that extend through the material from one surface to the other surface. Non-porous, as employed in this specification, thus means a material that is configured to prevent tissue growth through the implanted material.

Embodiments provide an incontinence treatment device provided with a non-porous support and an adjustment mechanism attached to the support. The non-porous support discourages or does not allow tissue to growth through the support such that the support will be able to move relative to the tissue long after having been implanted. The adjustment mechanism operates to adjust and move the non-porous support. The adjustment mechanism moves the support between a first position that allows the passage of urine and a second position that coapts the urethra. The adjustment mechanism is provided as an adjustment device that frictionally engages with a restrictor segment provided inside of a channel of an anchor. The adjustment device is adapted to be forced past the restrictor segment into the second position that is configured to tension the support and coapt the urethra.

Figure 1:
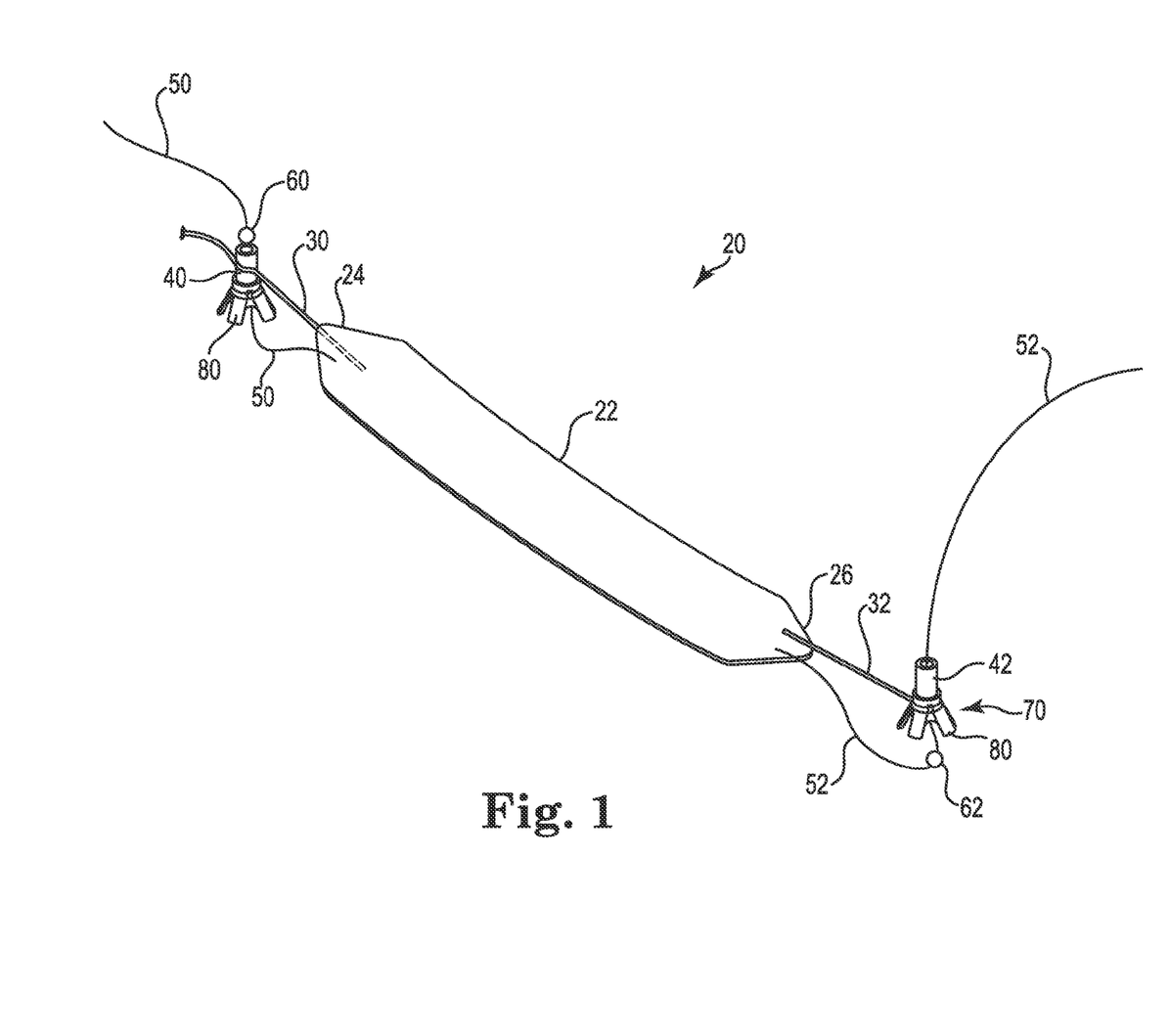
FIG. 1 is a perspective view of one embodiment of an incontinence treatment device provided with an anchor and an adjustment device.

FIG. 1 is a perspective view of one embodiment of an incontinence treatment device 20. The incontinence treatment device 20 (device 20) includes a sling 22 or a support 22 provided with tissue anchors 40, 42 and an adjustment mechanism 70. The tissue anchors 40, 42 fix the sling 22 into place within the pelvis and the adjustment mechanism 70 is accessible by the user/patient to adjust a position of the sling 22. The sling 22 is provided as a non-porous material that prevents body tissue from growing into or through the sling 22 after implantation. The adjustment mechanism 70 is operable to move the sling 22 relative to tissue to move the sling 22 between a first position that allows the passage of urine through the urethra and a second position that coapts the urethra.

The sling 22 includes a first end 24 and a second end 26. The device 20 includes a first extension member 30 attached to the first end 24 and a second extension member 32 attached to the second end 26 of the support 22, a first anchor 40 attached to the first extension member 30 and a second anchor 42 attached to the second extension member 32, with a first line 50 inserted through the first anchor 40 and a second line 52 inserted through the second anchor 42. The first line 50 is attached to the first end 24 of the sling 22 and is provided with a stop device 60. The first anchor 40 is positioned between the stop device 60 and the sling 22. The second line 52 is attached to the second end 26 of the sling 22 and is provided with an adjustment device 62. The adjustment device 62 is movable through a channel that is formed in the second anchor 42 such that the adjustment device 62 and the second anchor 40 combine to provide the adjustment mechanism 70.

The sling 22 is configured to be implanted into a user to support the urethra and treat incontinence. In one embodiment of the sling 22 is a sub-urethral sling 22 that is implanted under or inferior relative to the urethra. In one embodiment, each of the first and second anchors 40, 42 is fixed in position relative to the sling 22, for example by fixing a length of the first and second extension members 30, 32 and then connecting the anchors 40, 42 to a respective one of the members 30, 32. Adjustment of the device 20 is provided by the adjustment mechanism 70.

The adjustment mechanism 70 is operable to move the sling 22 between a first configuration that allows the user to pass urine and a second configuration that supports and coapts the urethra to provide the user with a continent state. In one embodiment, the adjustment mechanism 70 is user-operable long after the sling 22 has been implanted and the surgical site has healed. With this in mind, in one embodiment the sub-urethral sling 22 is provided as a non-porous film that is adapted to reduce or prevent tissue growth through the sling 22, which allows the sling 22 to move or slide relative to the tissue after implantation.

The sling 22 is suitably fabricated from polymer materials. For example, in one embodiment the sling 22 is a synthetic material fabricated from rubber, silicone, thermoplastic polymers, thermoset polymers, or blends or copolymers of suitable polymers. One suitable sling 22 is molded from silicone polymer.

The extension members 30, 32 are secured to the anchors 40, 42, respectively. The extension members 30, 32 and the anchors 40, 42 are fabricated from material that is suited for implantation into the human body. Preferably, the extension members 30, 32 and the anchors 40, 42 do not bio-absorb after implantation. As one example, the extension members 30, 32 and the anchors 40, 42 are suitably fabricated from polypropylene.

Each of the anchors 40, 42 is configured to be inserted into and engaged with tissue. In one embodiment, each anchor is provided with at least one projection 80 that extends away from a central axis of the anchor and is so configured to engage with tissue. In the illustrated embodiment, each of the anchors 40, 42 includes multiple projections 80—or wings—that configure each anchor 40, 42 to engage with tissue when implanted.

Figure 2:
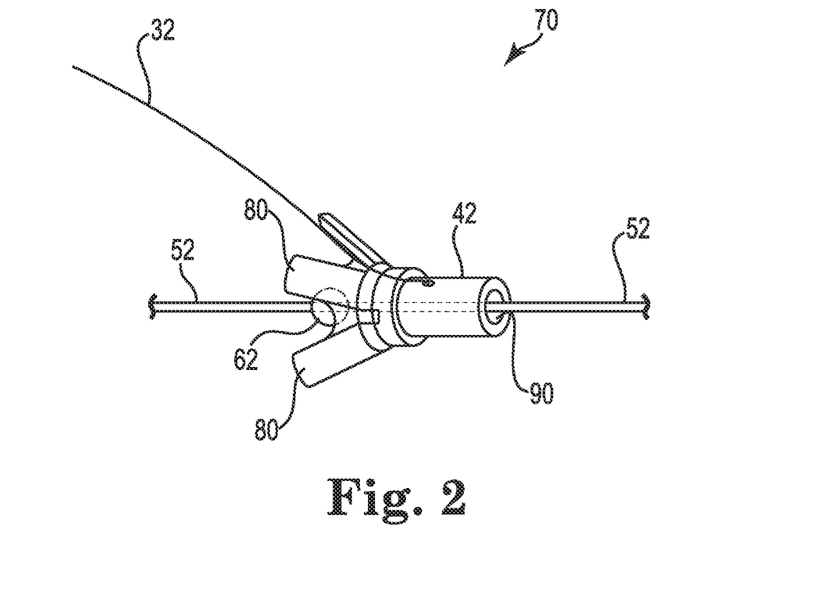
FIG. 2 is a perspective view of the anchor and the adjustment device illustrated in FIG. 1.
Figure 3:
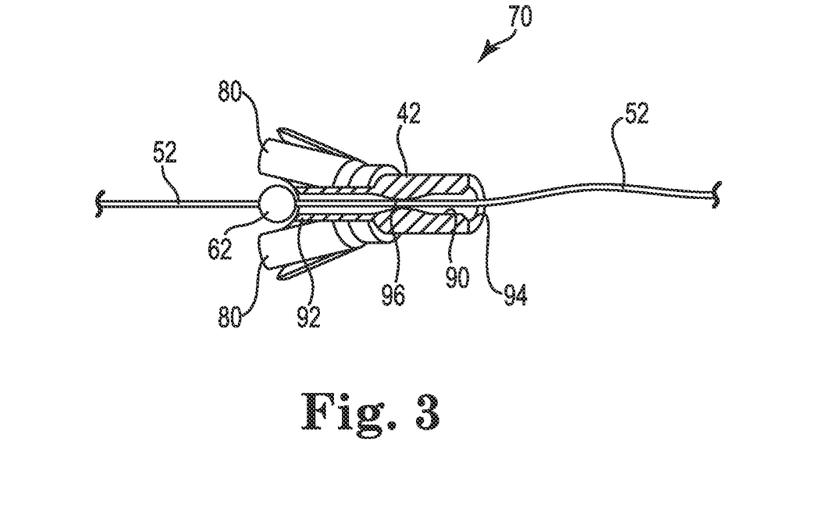
FIG. 3 is a cross-sectional view of the anchor and the adjustment device illustrated in FIG. 1.

FIG. 2 is a perspective view and FIG. 3 is a cross-sectional view of one embodiment of the adjustment mechanism 70. One of the anchors 40, 42, for example in this embodiment the second anchor 42, is provided with a channel 90 that extends between a first end 92 and a second end 94 of the anchor 42. The channel 90 is formed to include a restrictor segment 96 between the first and second ends 92, 94.

In one embodiment, the second extension member 32 is attached to an exterior surface of the second anchor 42. In one embodiment, the second extension member 32 is overmolded into a polymer wall of the second anchor 42.

The second line 52 is inserted through the channel 90 of the second anchor 42. The adjustment device 62 is sized to have a lateral dimension that is larger than a lateral dimension of the restrictor segment 96. In this manner, the adjustment device 62 is retained at the first end 92 of the anchor 42 when the adjustment mechanism 70 is in a first position that allows the user to urinate. The adjustment device 62 is adapted to be pulled through the restrictor segment 96 when force is applied to the second line 52, which pulls the adjustment device 62 from the first end 92 to the second end 94 of the anchor 42. The restrictor segment 96 is provided to maintain the adjustment device 62 adjacent to the second end 94 of the anchor 42 until the user applies a restoring force to the second line 52, at which point the adjustment device 62 moves back through the channel 90 to the first end 92 of the anchor 42. The selective placement of the adjustment device 62 adjacent to the second end 94 of the anchor 42 reduces an effective length of the sling 22, which operates to close down the urethra and provide the user with a continent state.

In one embodiment, the first and second extension members 30, 32 are secured to each of the respective anchors 40, 42 and these elements combine to provide the device 20 with a fixation mechanism that is configured to secure the sling 22 into tissue when implanted. The sling 22, when implanted, is thus suspended on a path having a path length that extends between the anchors 40, 42. The first and second lines 50, 52 are movable relative to the anchors 40, 42, respectively. In one embodiment, at least second line 52 is movable through the second anchor 42 to shorten the path length of the sling 22, which allows compression to be applied to the urethra to achieve a continent state as illustrated and described in FIGS. 4A and 4B below.

The lines 50, 52 are fabricated from material that is suited for implantation into the human body. Preferably, the lines 50, 52 do not bio-absorb after implantation. As one example, the lines are suitably fabricated from polypropylene.

Figure 4A:
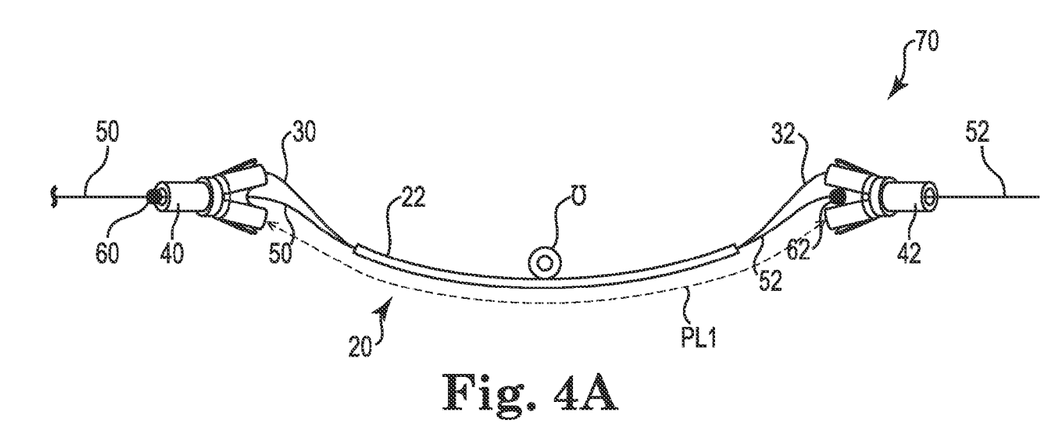
FIG. 4A is a schematic view of an incontinence treatment device implanted in the user and configured to allow the passage of urine.

FIG. 4A is a schematic view of the device 20 as implanted. When implanted, the non-porous structure of the sling 22 will resist and prevent tissue from growing through or attaching to the sling 22. Eventually, a protective pocket of epithelial tissue will grow around the device 20. The non-porous nature of the sling 22 allows portions of the device 20 to move within the pocket of tissue that surrounds the sling 22.

During implantation, the first and second anchors 40, 42 are fixed into tissue and the sling 22 is suspended along a path length PL1 that extends between the anchors 40, 42 under the urethra U. Although the anchors 40, 42 are fixed in the tissue, the non-porous sling 22 is free to move relative to the tissue. The adjustment mechanism 70 occupies a first position where the adjustment device 62 is located between the sling 22 and the second anchor 42. In the illustrated first position, the sling 22 is under the urethra U and the urethra U is not coapted, which allows the user to pass urine. The adjustment mechanism 70 operates to move the sling 22, which shortens the path length PL1, which tensions the sling 22 to coapt the urethra U as shown in FIG. 4B.

Figure 4B:
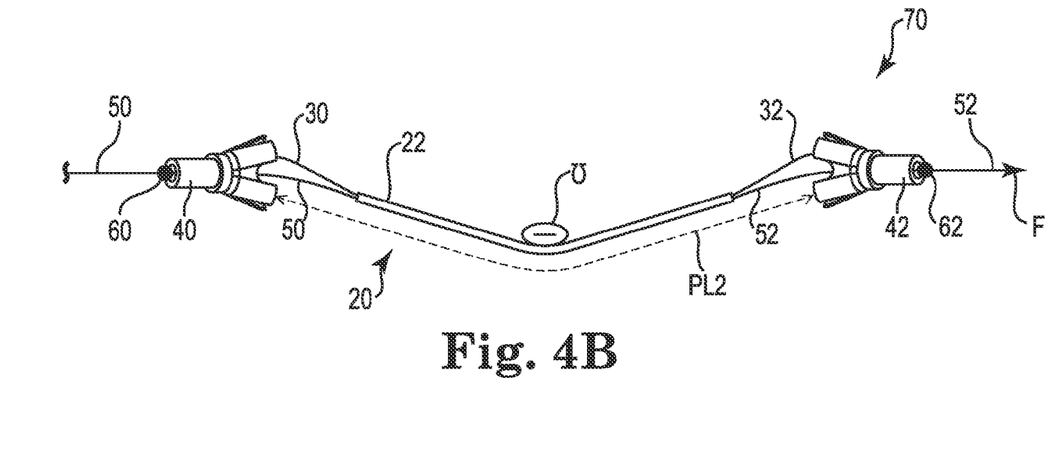
FIG. 4B is a schematic view of the incontinence treatment device illustrated in FIG. 4A adjusted to coapt a urethra of the user.

FIG. 4B is a schematic view of the device 20 with a force F applied to the second line 52 that is sufficient to draw the adjustment device 62 through the anchor 42. With additional reference to FIG. 3, the force F applied to the second line 52 pulls the adjustment device 62 through the restrictor segment 96 until the adjustment device 62 is seated on the second end 94 of the anchor 42. The selective placement of the adjustment device 62 through the anchor 42 to position the anchor 42 between the adjustment device 62 and the sling 22 moves the adjustment mechanism 70 into a second position that shortens the path length from PL1 to a shorter path length PL2. The shorter path length PL2 allows the sling 22 to compress and coapt the urethra U. In the illustrated second position, the sling 22 is tightened and effectively shortens a distance of the device 20 between the first and second anchors 40, 42, which coapts the urethra U to provide the user with a continent state.

Figure 5A:
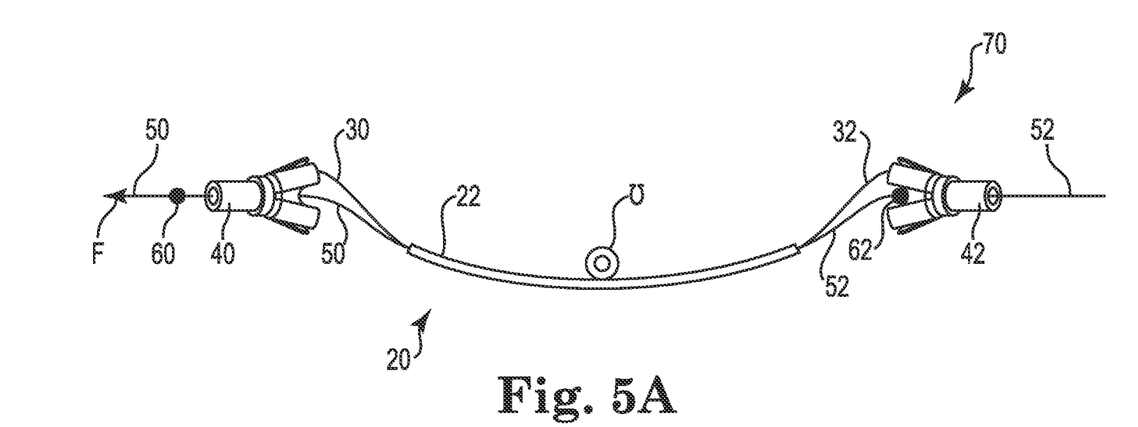
FIG. 5A and FIG. 5B illustrate various adjustment states for the incontinence treatment device illustrated in FIG. 4B.
Figure 5B:
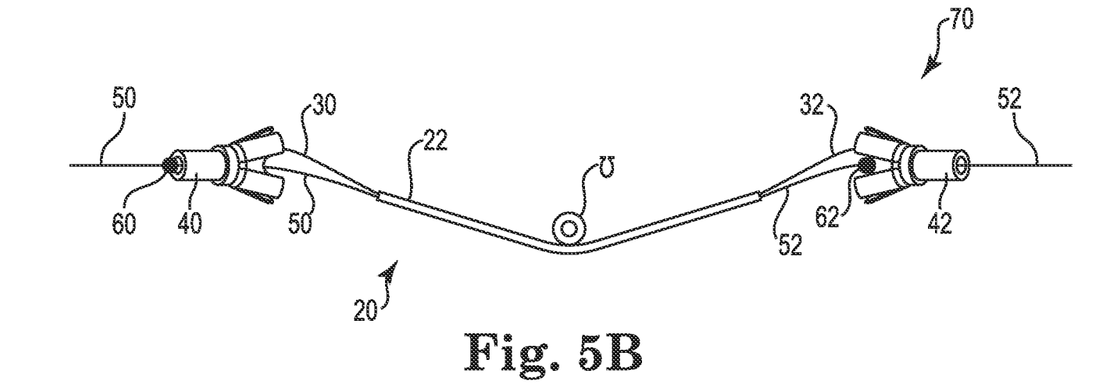

FIGS. 5A and 5B are schematic views of the device 20 with a force F applied to the first line 50 (FIG. 5A) to move the adjustment mechanism 70 from the second position back to the first position (FIG. 5B) to allow the user to pass urine. For example, the force F applied to the first line 50 draws the stop device 60 away from the first anchor 40 and pulls the adjustment device 62 back through the channel 90 (FIG. 3) formed in the anchor 42. In this manner, the adjustment device 62 is once again located between the sling 22 and the anchor 42, which loosens the sling 22. Placement of the adjustment device 62 between the sling 22 and anchor 42 effectively increases the distance of the device 20 between the anchors 40, 42. Increasing the effective distance of the device 20 relieves the tension in the sling 22, which relieves the constriction of the sling 22 against the urethra U to allow the urethra U to open and pass urine.

The incontinence treatment device 20 is implantable into the pelvis of the user. The adjustment mechanism 70 operates to allow the user to select a first configuration of the device 20 that allows urination or a second configuration that provides the user with a continent state.

In one embodiment, the first line 50 and the second line 52 are directed to a location outside the patient's body (for example through the abdominal wall or through the groin) to allow the user to access and selectively move the adjustment mechanism 70.

In one embodiment, the first line 50 and the second line 52 are directed to a location within the patient's body (for example within the scrotum or the labia) and also operate to provide the user with access to the adjustment mechanism 70.

Figure 6:
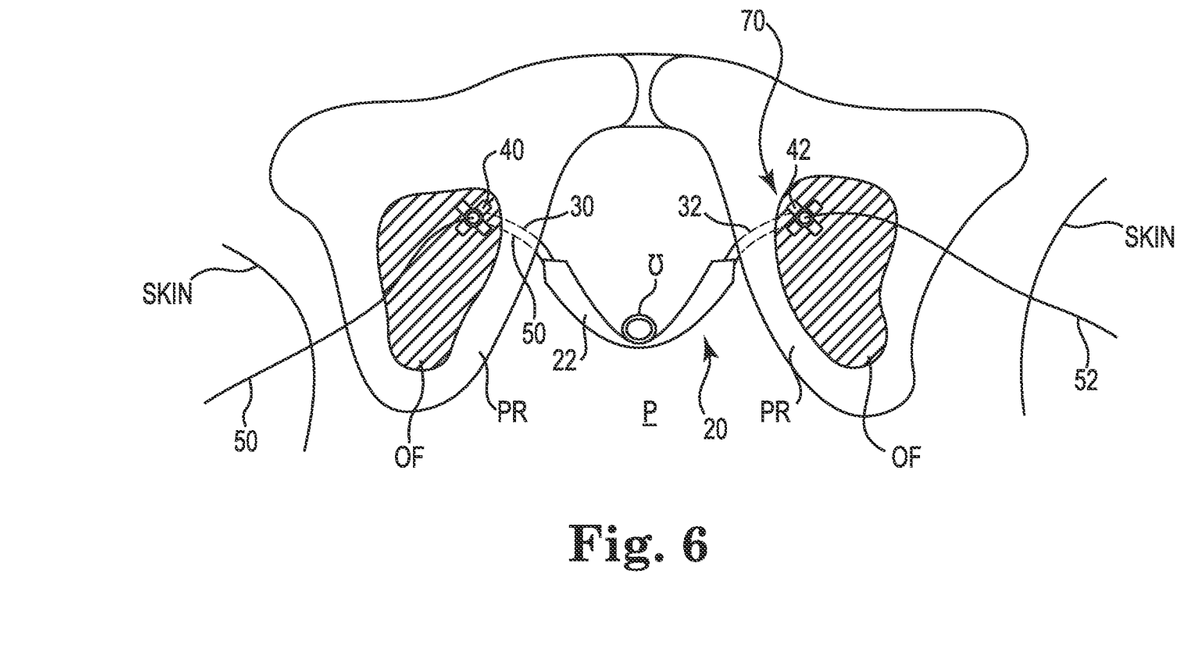
FIG. 6 is a schematic view of one embodiment of an incontinence treatment device implanted in a user.

FIG. 6 is a schematic view of the device 20 implanted within a pelvis P of a user. In one embodiment, each of the anchors 40, 42 is suitably implanted into a membrane of the obturator foramen OF to position the sling 22 under the urethra U. Each of the first and second lines 50, 52 are directed through the skin of the patient to a location outside the body that permits the user to adjust the adjustment mechanism 70 and move the urethra U between open and closed positions. A suitable antibiotic or barrier at the skin is employed to prevent the migration of bacteria along the lines 50, 52 into the patient's body.

The device 20 is configured to be implanted into the patient through a single incision. In one exemplary approach, a single incision is made near the urethra and tissue is dissected to expose the urethra U. A suitable introducer tool is employed to direct the first anchor 40 into the membrane covering the first obturator foramen OF and to permit the first line 50 to trail through the skin to a location outside of the body. A similar introducer tool is employed on the contralateral side of the body to place the second anchor 42 into the membrane covering the second obturator foramen OF and pass the second line 52 through the skin to a location outside of the body. In one suitable implantation procedure, the incision is made to expose the urethra (a vaginal incision for a female or a perineal incision for a male) and the introducer tool is moved from an "outside in" path from the groin, through the membrane over the obturator foramen OF, around the descending pubic ramus PR, and out of the incision for engagement with the first line 50 and the first anchor 40. The introducer tool that is now attached to the first line 50 and the first anchor 40 is pulled back along its pathway around the descending pubic ramus PR, through the obturator foramen OF, and out of the skin. A similar "outside in" path is employed on the contralateral side of the body to place the second line 52 and the second anchor 42.

Figure 7:
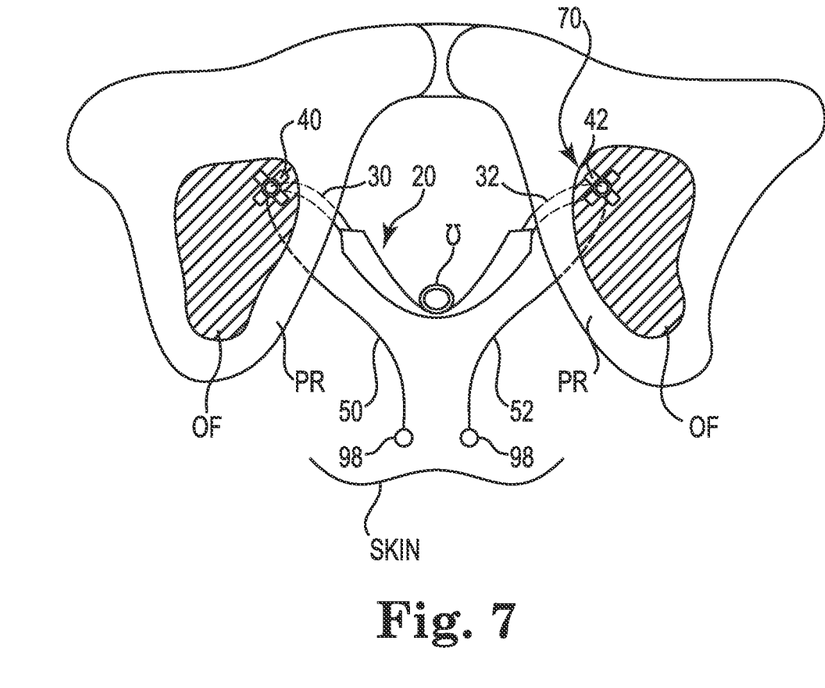
FIG. 7 is a schematic view of one embodiment of an incontinence treatment device planted in a user.

FIG. 7 is a perspective view of the device 20 implanted in a pelvis P of the user with the first and second lines 50, 52 implanted under the skin and in the body of the user. In one embodiment, the anchors 40, 42 are secured within the tissue covering the obturator foramen OF to suspend the sling 22 under the urethra U. In one embodiment, each of the first and second lines 50, 52 is suitably tunneled to a location inside the body such as within the skin of the scrotum or within the labia of a female user. It is desirable that the user is able to apply a force the both the first line 50 and the second line 52. With this in mind, a grasping device 98 is attached to an end of each of the lines 50, 52 to allow the user to apply a pulling force along the lines 50, 52 to move the adjustment mechanism 70 and open/close the urethra U.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. An incontinence treatment device comprising:
a non-porous sub-urethral sling;
a first extension member attached to a first end of the sling;
a first anchor attached to the first extension member;
a first line attached to the first end of the sling and inserted through a bore formed through the first anchor, the first line including a stop device fixed to the first line with the first anchor positioned between the stop device and the sling;
a second extension member attached to a second end of the sling;
a second anchor attached to the second extension member, the second anchor including a channel formed through the second anchor and a restrictor segment provided in the channel; and
a second line attached to the second end of the sling and inserted through the channel, the second line including an adjustment device attached to the second line that is movable through the channel formed through the second anchor;
wherein the restrictor segment is configured to resist movement of the adjustment device through the channel;

wherein the adjustment device is movable through the channel from a first position that locates the adjustment device between the second anchor and the sling to a second position that locates the second anchor between the adjustment device and the sling to thereby tighten the sling by shortening an effective distance of the device between the first and second anchors.

2. The incontinence treatment device of claim 1, wherein the non-porous sub-urethral sling is a substantially solid film that is adapted to reduce tissue growth onto a surface of the non-porous sub-urethral sling.

3. The incontinence treatment device of claim 1, wherein each of the first and second anchors includes at least one protrusion projecting outward relative to a central axis of the anchor that is configured to engage with tissue.

4. The incontinence treatment device of claim 1, wherein a maximum lateral dimension of the adjustment device is larger than a maximum lateral dimension of the restrictor segment.

5. The incontinence treatment device of claim 1, wherein the channel is formed through the second anchor between opposed ends of the second anchor and the restrictor segment is provided in the channel at an approximate midpoint between the opposed ends of the second anchor.

6. The incontinence treatment device of claim 1, wherein the second anchor has a first end and a second end, the first end disposed nearer to the sub-urethral sling than the second end, and the adjustment device is movable through the channel from the first end to the second end and the restrictor segment is configured to resist movement of the adjustment device from the second end to the first end of the second anchor.

7. The incontinence treatment device of claim 1, wherein the adjustment device is movable through the channel from the second position to the first position to thereby loosen the sling by increasing the effective distance of the device between the first and second anchors.

8. The incontinence treatment device of claim 1, wherein each of the first and second anchors includes at least two tissue engagement wings that configure each anchor for insertion into a membrane covering an obturator foramen of a user.

9. The incontinence treatment device of claim 1, wherein the first line is parallel to the first extension member and the second line is parallel to the second extension member.

10. The incontinence treatment device of claim 1, wherein the first line is coaxial with the first anchor and the second line is coaxial with the second anchor.

\* \* \* \* \*